United States Patent [19]

Brooks et al.

[11] Patent Number: 5,326,787

[45] Date of Patent: Jul. 5, 1994

[54] CYCLOALKYL N-HYDROXY DERIVATIVES HAVING LIPOXYGENASE INHIBITORY ACTIVITY

[75] Inventors: Dee W. Brooks, Libertyville; Jimmie L. Moore, Gurnee, both of Ill.; Karen E. Rodriques, Stow, Mass.

[73] Assignee: Abbott Laboratories, Abbott Park, Ill.

[21] Appl. No.: 111,764

[22] Filed: Aug. 25, 1993

Related U.S. Application Data

[63] Continuation of Ser. No. 883,618, May 12, 1992, abandoned.

[51] Int. Cl.$^5$ .............................................. A01N 55/02
[52] U.S. Cl. ..................................... 514/507; 562/623; 562/624
[58] Field of Search .......................... 562/624; 514/507

[56] References Cited

U.S. PATENT DOCUMENTS

| | | | |
|---|---|---|---|
| 4,299,778 | 11/1981 | Pilgram | 562/623 |
| 4,728,670 | 3/1988 | Haslanges et al. | 514/507 |
| 5,155,127 | 10/1992 | Trivedi | 514/507 |
| 5,214,204 | 5/1993 | Dellaria et al. | 562/623 |

FOREIGN PATENT DOCUMENTS

| | | | |
|---|---|---|---|
| 0320000 | 6/1989 | European Pat. Off. | 562/623 |
| 0384594 | 8/1990 | European Pat. Off. | 562/623 |
| 1135890 | 9/1962 | Fed. Rep. of Germany | 562/623 |
| 4193857 | 7/1992 | Japan | 562/623 |
| 2033378 | 5/1980 | United Kingdom | 514/507 |

OTHER PUBLICATIONS

Summers, "Preparation of Urea-based Lipoxygenes inhibiting compounds" EP 292699A2. Nov. 30, 1989; CA110(19):172898e. Abstract Only.

Summers et al, "Structure-activity analysis of a clsss of orally active hydroxamic acid inhibitors of Leukotriene biosynthesis", J. Med. Chem. 31(10), 1960–4 (1988) Chemical Abstract citation only (CA109(17):1490129.).

Primary Examiner—Jose'G. Dees
Assistant Examiner—Keith MacMillan
Attorney, Agent, or Firm—Jerry F. Janssen

[57] ABSTRACT

Compounds of the structure

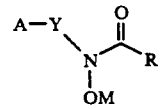

where M is hydrogen, a pharmaceutically acceptable cation or metabolically cleavable group, R is alkyl, cycloalkyl, or NR$^1$R$^2$, where R$^1$ and R$^2$ are hydrogen, alkyl, cycloalkyl alkonyl, or carbocyclic aryl, Y is alkylene, alkenylene, or cyclopropyl, and A is optionally substituted cycloalkyl or cycloalkylene are potent inhibitors of lipoxygenase enzymes and thus inhibit the biosynthesis of leukotrienes. These compounds are useful in the treatment or amelioration of allergic and inflammatory disease states.

5 Claims, No Drawings

CYCLOALKYL N-HYDROXY DERIVATIVES HAVING LIPOXYGENASE INHIBITORY ACTIVITY

This application is a continuation of U.S. patent application Ser. No. 07/883,618, filed May 12, 1992 now abandoned.

TECHNICAL FIELD

This invention relates to compounds having biological activity to inhibit lipoxygenase enzymes, to pharmaceutical compositions comprising these compounds, and to a medical method of treatment. More particularly, this invention concerns certain cycloalkyl N-hydroxyureas and hydroxamic acids which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain substituted cycloalkyl compounds which inhibit lipoxygenase enzyme activity and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The compounds of this invention have the structure

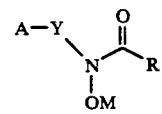

or a pharmaceutically acceptable salt thereof wherein the group M represents hydrogen, a pharmaceutically acceptable cation, or a pharmaceutically acceptable metabolically cleavable group.

The group R is selected from hydrogen, alkyl of from one to twelve carbon atoms, cycloalkyl of from three to eight carbon atoms, and $-NR^1R^2$. In the group $-NR^1R^2$, $R^1$ is selected from the group consisting of hydrogen, hydroxy, alkyl of from one to six carbon atoms, hydroxyalkyl of from one to six carbon atoms, and alkoxyalkyl in which the alkoxy portion and the alkyl portion each contain, independently, from one to six carbon atoms; and $R^2$ is selected from the group consisting of hydrogen, alkyl of from one to six carbon atoms, hydroxyalkyl of from one to six carbon atoms, alkoxyalkyl in which the alkoxy portion and the alkyl portion each contain, independently, from one to six carbon atoms, alkanoyl of from two to eight carbon atoms, alkyl(carbocyclic aryl) in which the alkyl portion contains from one to six carbon atoms, and carbocyclic aryl.

The group A is selected from the group consisting of cycloalkyl or cycloalkylene of from three to eight carbon atoms or optionally substituted cycloalkyl or cycloalkylene. The optional substituents are selected from the group consisting of alkyl of from one to six carbon atoms, haloalkyl of from one to six carbon atoms, alkoxy of from one to six carbon atoms, alkoxyalkyl as defined above, hydroxy, halogen, carboxylic ester, alkyl carboxylic ester and hydroxyalkyl.

The group Y represents $C_1-C_6$ alkylene or alkenylene or cyclopropyl, with the provisio that when A is cyclopropyl then Y is not alkylene.

In another embodiment, the present invention provides pharmaceutical compositions which comprise a therapeutically effective amount of compound as defined above in combination with a pharmaceutically acceptable carrier.

In a still further embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "metabolically cleavable group" denotes a group which is cleaved in vivo to yield the parent molecule of the structural formulae indicated above wherein M is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$-C$_4$ alkyl, halogen, hydroxy or C$_1$-C$_4$ alkoxy. Specific examples of representative metabolically cleavable groups include acetyl, methoxycarbonyl, benzoyl, methoxymethyl and trimethylsilyl groups.

PREFERRED EMBODIMENTS

Preferred compounds of the present invention are those having the structure.

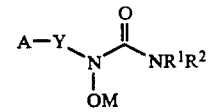

where the values of A, Y, M, R$^1$, and R$^2$ are as defined above. Particular compounds falling within the scope of the present invention include, but are not limited to:

N-1-(trans-2-cyclopropylcyclopropylmethyl)-N-hydroxyurea;
N-cycolbutylmethyl-N-hydroxyurea;
N-cyclopentylmethyl-N-hydroxyurea;
N-cyclohexylmethyl-N-hydroxyurea;
N-cycloheptylmethyl-N-hydroxyurea;
N-1-(trans-2-cyclopropylcyclopropylethyl)-N-hydroxyurea;
N-1-(trans-2-cyclopropylcyclopropylethyl)-N-hydroxy-N'-methylurea;
N-1-(trans-2-cyclopropylcyclopropylethyl)-N-hydroxy-N'-phenylurea;
N-1-(trans-2-cyclopropylcyclopropylethyl)-N-hydroxy-N'-cyclohexylurea;
N-1-(trans-2-cyclopropylcyclopropylethyl)-N-hydroxyacetamide.

Certain compounds of this invention may exist in either cis or trans isomers with respect to the relationship of the two groups attached to the cycloalkyl cycloalkenyl ring in addition to stereoisomeric forms which arise by virtue of the presence of one or more chiral centers. The present invention contemplates all such geometric and stereoisomers, including R- and S-enantiomers, diastereomers, and cis/trans mixtures thereof as falling within the scope of the invention. If a particular enantiomer is desired, it may be prepared by chiral synthesis or by derivatization with a chiral auxiliary where the resulting diastereomeric mixture is separated and the auxiliary group cleaved to provide the desired pure enantiomers.

LIPOXYGENASE INHIBITION DETERMINATION

Inhibition of leukotriene biosynthesis was evaluated in an assay, involving calcium ionophore-induced LTB$_4$ biosynthesis expressed human whole blood. Human heparinized whole blood was preincubated with test compounds or vehicle for 15 min at 37° C. followed by calcium ionophore A23187 challenge (final concentration of 8.3 μM) and the reaction terminated after 30 min by adding two volumes of methanol containing prostaglandin B$_2$ as an internal recovery standard. The methanol extract was analyzed for LTB$_4$ using a commercially available radioimmunoassay.

The compounds of this invention inhibit leukotriene biosynthesis as illustrated in Table 1.

TABLE 1

| In Vitro Inhibitory Potencies of Compounds of this Invention Against 5-Lipoxygenase from Stimulated LTB$_4$ Formation in Human Whole Blood | |
|---|---|
| Example | IC$_{50}$ (10$^{-6}$ M) |
| 1 | <0.3 |

TABLE 1-continued

In Vitro Inhibitory Potencies of Compounds of this Invention Against 5-Lipoxygenase from Stimulated LTB$_4$ Formation in Human Whole Blood

| Example | IC$_{50}$ (10$^{-6}$ M) |
|---|---|
| 2 | 0.9 |
| 3 | 0.7 |
| 4 | 1.1 |
| 5 | <1.5 |

INHIBITION OF LEUKOTRIENE BIOSYNTHESIS

Inhibition of the biosynthesis of leukotrienes in vivo after oral administration of compound was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results are presented in Table 2.

TABLE 2

In Vitro Inhibitory Potencies of Compounds of this Invention

| Example | Inhibition of Leukotriene at 100 μmoles/kg |
|---|---|
| 1 | 96 |
| 2 | 92 |
| 3 | 83 |
| 4 | 64 |

PHARMACEUTICAL COMPOSITIONS

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

PREPARATION OF COMPOUNDS OF THIS INVENTION

The compounds of this invention can be prepared as is illustrated in Scheme 1. The requisite carbonyl intermediate I is converted to the corresponding hydroxylamine II by known methods. The hydroxylamine II is converted to the desired N-hydroxyureas III by treatment with isocyanates or HCNO in the case where $R^1$ is hydrogen. The hydroxylamine II is converted to the desired hydroxamic acid IV by reaction with an acylchloride in the presence of a suitable base followed by selective hydrolysis of the intermediate N,O-diacylhydroxylamine.

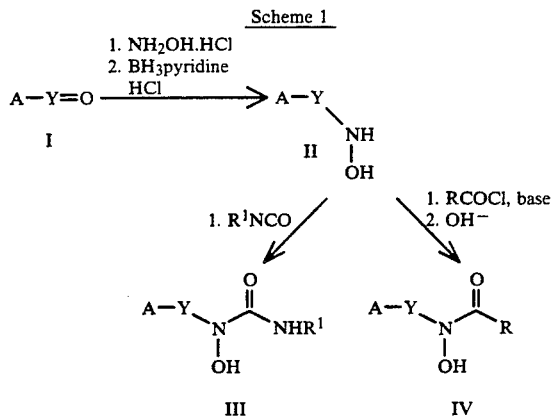

The compounds of this invention can also be prepared as is illustrated in Scheme 2. The requisite hydroxyl intermediate V is converted to the corresponding diphenoxycarbonyl hydroxylamine derivative VII by treatment with triphenylphospine and diethylazodicarboxylate and reagent VI. Treatment of intermediate VII with an amine $NH_2R^1$ provides the desired N-hydroxyurea III.

Scheme 2

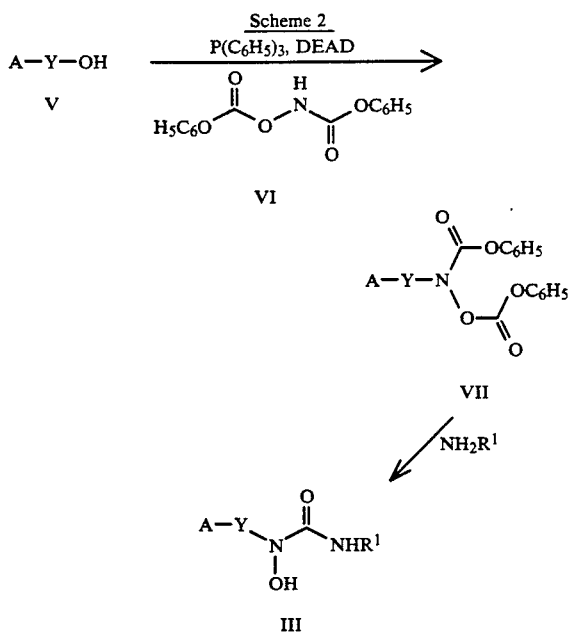

EXAMPLE 1

Preparation of N-1-(trans-2-cyclopropylcyclopropylmethyl)-N-hydroxyurea

A solution of cyclopropanecarboxaldehyde (5.00 g, 71.3 mmol) and (carbethoxymethylene)triphenylphosphorane (26.09 g, 74.9 mmol) in toluene (250 mL) was heated at reflux for 6 hours. The mixture was cooled to ambient temperature and concentrated in vacuo. The resulting residue was taken up in ether (500 mL) and the triphenylphosphine oxide was filtered off. The filtrate was concentrated to afford a 9:1 mixture of trans:cis ethyl 3-cyclopropylpropenoate which was used as is.

A solution of the mixture of ethyl 3-cyclopropylpropenoate from above in 1:1 THF:1N LiOH (250 mL) was stirred for 72 hours. The THF was then stripped off in vacuo and the remaining aqueous solution was washed with ether (2×50 mL). It was then acidified to pH 2 by the addition of concentrated HCl and extracted with ethyl acetate (3×50 mL). These last organics were combined, dried over MgSO4 and concentrated to afford 8.15 g of a mixture of 9:1 trans:cis 3-cyclopropylpropenoic acid as an off white solid which was used as is.

To a solution of the 3-cyclopropylpropenoic acid mixture from above in CH2Cl2 (250 mL) was added oxalyl chloride (10.86 g, 85.56 mmol) followed by one drop of N,N-dimethylformamide and the reaction was stirred for 1 hour. It was then concentrated in vacuo. The resulting residue was taken up in fresh CH2Cl2 (250 mL) and cooled to 0° C. N,O-Dimethylhydroxylamine hydrochloride (8.35 g, 85.56 mmol) was added followed by the dropwise addition of pyridine (13.54 g, 171.12 mmol). The cooling bath was withdrawn and the reaction allowed to warm to ambient temperature. It was then diluted with brine (200 mL) and the layers were separated. The aqueous phase was extracted with CH2Cl2 (2×200 mL). The organics were combined, dried over MgSO4 and concentrated. The resulting residue was chromatographed (silica gel, ether:hexanes, 3:2) to afford 9.52 g (86% over three steps) of a 95:5 mixture of trans:cis 3-cyclopropyl-N,O-dimethylpropenamide as a colorless oil.

To a solution of trimethylsulfoxonium iodide (14.85 g, 67.5 mmol) in DMSO (200 mL) was added NaH (1.67 g of a 97% dry sample, 67.5 mmol) and the mixture was stirred for 20 min. The 3-cyclopropyl-N,O-dimethylpropenamide mixture (9.51 g, 61.4 mmol) from above was added dropwise as a solution in DMSO (50 mL). Upon completion of addition, the reaction was stirred for 2 hours at ambient temperature followed by heating at 50° C. for an additional 1 hour. It was then cooled to ambient temperature and diluted with brine (500 mL). This aqueous solution was extracted with ethyl acetate (3×300 mL). The organics were combined, dried over MgSO4 and concentrated. The resulting residue was chromatographed (silica gel, ether:hexanes, 1:1) to afford 8.24 g (79%) of trans-2-cyclopropyl-N,O-dimethylcyclopropylamide as a colorless oil.

To a solution of trans-2-cyclopropyl-N,O-dimethylcyclopropylamide (8.23 g, 48.7 mmol) in THF (200 mL) at 0° C. was added diisobutylaluminumhydride (48.7 mL of a 1.0M solution in hexanes, 48.7 mmol). Upon completion of addition, the reaction was stirred for 30 min at 0° C. It was then quenched with saturated aqueous NH4Cl solution (200 mL) and extracted with ethyl acetate (3×200 mL). The organics were combined, dried over MgSO4 and concentrated to afford trans-2-cyclopropylcyclopropylcarboxaldehyde which was used as is.

A solution of trans-2-cyclopropylcyclopropylcarboxaldehyde from above and hydroxylamine hydrochloride (3.72 g, 53.7 mmol) in 1:1 ethanol:pyridine (240 mL) was stirred for 18 hours. It was then concentrated in vacuo. The residue was taken up in brine (200 mL) and extracted with ethyl acetate (3×200 mL). The organics were combined, dried over MgSO4 and concentrated to afford trans-2-cyclopropylcyclopropyl carboxaldehyde oxime which was used as is.

To a solution of trans-2-cyclopropylcyclopropylcarboxaldehyde oxime from above, in ethanol (200 mL) was added borane-pyridine (9.96 g, 107.14 mmol) and the mixture was stirred for 30 min. HCl (24.35 mL of a 6N solution, 146.1 mmol) was then added dropwise and the reaction was stirred for 1.5 hours. It was then neutralized by the addition of 2N aqueous NaOH and concentrated in vacuo. The residue was further diluted with brine (100 mL) and extracted with ethyl acetate (3×150 mL). The organics were combined, dried over MgSO4 and concentrated to afford N-(2-trans-cyclopropylcyclopropylmethyl)-N-hydroxylamine which was used as is.

To a solution of hydroxylamine intermediate from above, in THF (200 mL) was added trimethylsilylisocyanate (5.89 g, 51.14 mmol) and the reaction was stirred for 10 min. It was then concentrated in vacuo. The resulting residue was chromatographed (silica gel, ether:hexanes to ether methanol, 7:3 to 9:1) followed by crystallization in ethyl acetate/hexanes to afford N-1-(trans-2-cyclopropylcyclopropylmethyl)-N-hydroxyurea. m.p.=121.5°–122.5° C.; $^1$H NMR (300 MHz, DMSO-d$_6$): δ0.14–0.33 (m, 5H), 0.77 (m, 4H), 3.16 (m, 2H), 6.23 (bs, 2), 9.17 (s, 1H); Mass Spectrum (DCI/NH$_3$): (M+NH$_4$)$^+$=188; Analysis calc'd for C$_8$H$_{14}$N$_2$O$_2$: C, 56.45, H, 8.29, N, 16.46; Found: C, 56.33, H, 8.24, N, 16.37.

EXAMPLE 2

Preparation of N-cyclobutylmethyl-N-hydroxyurea

To a solution of oxalyl chloride (10.17 g, 80.1 mmol) in $CH_2Cl_2$ (250 mL) at $-78°$ C., was added DMSO (13.07 g, 167.3 mmol) dropwise and the resulting mixture was stirred for 5 min. A solution of cyclobutanemethanol (6.00 g, 69.7 mmol) in $CH_2Cl_2$ (20 mL) was then added dropwise and the reaction was stirred for 20 min at $-78°$ C. Triethylamine (35.20 g, 348.5 mmol) was then added dropwise. Upon completion of addition, the cooling bath was withdrawn and the reaction allowed to warm to ambient temperature. It was then diluted with brine (250 mL) and the layers separated. The aqueous phase was extracted with $CH_2Cl_2$ (2×200 mL). The organics were combined, dried over $MgSO_4$ and concentrated. The resulting residue was taken up in ether (500 mL) and the triethylamine hydrochloride filtered off. The filtrated was concentrated to afford cyclobutanecarboxaldehyde which was used as is.

The desired material was prepared according to the procedure of Example 1 substituting cyclobutanecarboxaldehyde for trans-2-cyclopropylcyclopropyl carboxaldehyde. m.p.=112°–113° C.; $^1$H NMR (300 MHz, DMSO-$d_6$): δ1.68 (m, 2H), 1.80 (m, 2H), 1.97 (m, 2H), 2.55 (m, 1H), 3.34 (d, 2H, J=7 Hz), 6.20 (bs, 2H), 9.13 (s, 1H); Mass Spectrum (DCI/$NH_3$): $(M+H)^+ = 145$; Analysis calc'c for C6H12N2O2: C, 49.98, H, 8.39, N, 19.43; Found: C, 49.35, H, 8.11, N, 19.60.

EXAMPLE 3

Preparation of N-cyclopentylmethyl-N-hydroxyurea

The desired material was prepared according to the procedure of Example 2 substituting cyclopentanemethanol for cyclobutanemethanol m.p.=115°–116° C.; $^1$H NMR (300 MHz, DMSO-$d_6$): δ1.19 (m, 2H), 1.51 (m, 4H), 1.64 (m, 2H), 2.18 (m, 1H), 3.24 (d, 2H, J=7 Hz), 6.20 (bs, 2H), 9.17 (s, 1H); Mass Spectrum (DCI/$NH_3$): $(M+H)^+ = 159$; Analysis calc'd for C7H14N2O2: C, 53.14, H, 8.92, N, 17.71; Found: C, 53.26, H, 8.99, N, 17.76.

EXAMPLE 4

Preparation of N-hydroxy-N-1-(1-cyclohexyl)methylurea

A solution of cyclohexanecarboxaldehyde (11.2 g, 100 mmol), hydroxylamine hydrochloride (7.2 g, 104 mmol) and pyridine (8.5 mL) in ethanol (150 mL) was stirred for 18 hours, then concentrated in vacuo. The residue was taken up in 10% aqueous citric acid and extracted with ethyl acetate (3×150 mL). The organics were combined, dried over $MgSO_4$ and concentrated to afford cyclohexanecarboxaldehyde oxime which was used directly in the next step.

To a solution of cyclohexanecarboxaldehyde oxime from above, in glacial acetic acid (50 mL) was added sodium cyanoborohydride (12.5 g, 199 mmol) and the mixture was stirred for 18 hours, then concentrated in vacuo. It was then treated with crushed ice and neutralized by the addition of aqueous 4N NaOH and extracted with ethyl acetate (5×150 mL). The organics were combined, dried over $MgSO_4$ and concentrated to afford cyclohexylmethyl)-N-hydroxylamine which was used as is.

To a solution of hydroxylamine intermediate from above, in THF (200 mL) was added trimethylsilylisocyanate (5.89 g, 51.14 mmol) and the reaction was stirred for 10 min. It was then concentrated in vacuo. The resulting residue was chromatographed (silica gel, ethyl acetate:hexanes, 7:3 to 9:1) followed by crystallization in ethyl acetate/hexanes to afford N-hydroxy-N-1-(1-cyclohexyl)methylurea.

m.p.=143°–144.5° C.; $^1$H NMR (300 MHz, DMSO-$d_6$): δ0.86 (m, 2H), 1.16 (m, 3H), 1.65 (m, 6H), 3.16 (d, 2H, J=6.6), 6.15 (bs, 2H), 9.16 (s, 1H); Analysis calc'd for C8H16N2O2: C, 55.79, H, 9.36, N, 16.27; Found: C, 55.60, H, 9.34, N, 16.17.

EXAMPLE 5

Preparation of N-hydroxy-N-1-(1-cycloheptyl)methylurea

To a stirred solution of cycloheptanemethanol (11.2 g, 100 mmol), tert-butyl N-(tert-butoxycarbonyloxy)-carbamate (7.2 g, 104 mmol) and triphenylphosphine (7.2 g, 104 mmol) in THF (150 mL) was added diethylazodicarboxylate dropwise. The mildly exothermic reaction was stirred 3 hours, then concentrated in vacuo. The concentrate was treated with hexane, and the crystalline by-product was vacuum filtered. The filtrate was concentrated in vacuo and the resulting residue was chromatographed (silica gel, ethyl acetate:hexanes, 2:8) to afford the protected hydroxylamine derivative.

To a solution of protected hydroxylamine derivative from above (19.5 g, 56.8 mmol) in methanol (125 mL) was added powdered anhydrous potassium carbonate (12.5 g, 116 mmol) and the mixture was stirred for 18 hours, then concentrated in vacuo. It was then treated with 10% aqueous citric acid and extracted with ethyl acetate 3×150 mL). The organics were combined, dried over $MgSO_4$ and concentrated in vacuo. The residue was chromatographed (silica gel, ethyl acetate:hexanes, 20:80) to afford pure tert-butyl N-hydroxy-N-1-(1-cycloheptyl)methylcarbamate.

To a solution of carbamate derivative from above (10.5 g, 43.1 mmol) in glacial acetic acid was added aqueous 6N HCl (11 mL) and the mixture was stirred for 2.5 hours. It was then treated with crushed ice and basified with aqueous 4N NaOH and the aqueous mixture extracted with ethyl acetate (4×120 mL). The organics were combined, dried over $MgSO_4$ and concentrated in vacuo to afford N-1-(1-cycloheptyl)methylhydroxylamine, which was used directly in the next step.

To a solution of hydroxylamine (3.0 g, 20.9 mmol) from above, in THF (25 mL) was added trimethylsilylisocyanate (2.9 g, 25.2 mmol) and the reaction was stirred for 30 min. The reaction was treated with saturated aqueous $NH_4Cl$ and the aqueous mixture extracted with ethyl acetate (4×120 mL). The organics were combined, dried over $MgSO_4$ then concentrated in vacuo. The resulting residue was chromatographed (silica gel, ethyl acetate:hexanes, 50:50) followed by crystallization in ethyl acetate/hexanes to afford N-hydroxy-N-1-(1-cycloheptyl)methylurea.

m.p.=110°–112° C.; $^1$H NMR (300 MHz, DMSO-$d_6$): δ1.09 (m, 2H), 1.2–1.7 (m, 10H), 1.79 (m, 1H), 3.14 (d, 2H, J=7.4), 6.16 (bs, 2H), 9.17 (s, 1H); Analysis calc'd for C9H18N2O2: C, 58.04, H, 9.74, N, 15.04; Found: C, 57.85, H, 9.60, N, 15.10.

EXAMPLE 6

Preparation of
N-1-(trans-2-(cyclopropyl)cyclopropylethyl)-N-hydroxyurea

The desired material is prepared according to the procedure of Example 1 substituting trans-2-cyclopropylcyclopropyl methyl ketone for trans-2-cyclopropylcyclopropyl carboxaldehyde.

EXAMPLE 7

Preparation of
N-1-(trans-2-(cyclopropyl)cyclopropylethyl)-N-hydroxy-N'-methylurea The desired material is prepared according to the procedure of Example 1 substituting trans-2-cyclopropylcyclopropyl methyl ketone for trans-2-cyclopropylcyclopropyl carboxaldehyde and methylisocyanate for trimethylsilylisocyanate.

EXAMPLE 8

Preparation of
N-1-(trans-2-(cyclopropyl)cyclopropylethyl)-N-hydroxy-N'-phenylurea The desired material is prepared according to the procedure of Example 1 substituting trans-2-cyclopropylcyclopropyl methyl ketone for trans-2-cyclopropylcyclopropyl carboxaldehyde and phenylisocyanate for trimethylsilylisocyanate.

EXAMPLE 9

Preparation of
N-1-(trans-2-(cyclopropyl)cyclopropylethyl)-N-hydroxy-N'-phenylurea The desired material is prepared according to the procedure of Example 1 substituting trans-2-cyclopropylcyclopropyl methyl ketone for trans-2-cyclopropylcyclopropyl carboxaldehyde and cyclohexylisocyanate for trimethylsilylisocyanate.

EXAMPLE 10

Preparation of
N-1-(trans-2-(cyclopropyl)cyclopropylethyl)-N-hydroxyacetamide

The desired material is prepared according to the procedure of Example 1 substituting trans-2-cyclopropylcyclopropyl methyl ketone for trans-2-cyclopropylcyclopropyl carboxaldehyde and acetyl chloride for trimethylsilylisocyanate.

The compounds represented in Table 3 can be prepared by the method as described in Example 1 substituting the appropriate carbonyl precursor shown by molecular formula instead of trans-2-cyclopropylcyclopropyl carboxaldehyde.

TABLE 3

| Example | Carbonyl Precursor | Product |
|---|---|---|
| 11 | | |
| 12 | | |
| 13 | | |
| 14 | | |
| 15 | | |

TABLE 3-continued
| Example | Carbonyl Precursor | Product |
|---|---|---|
| 16 | 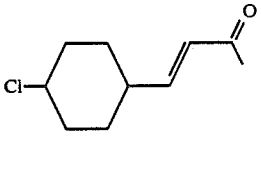 | 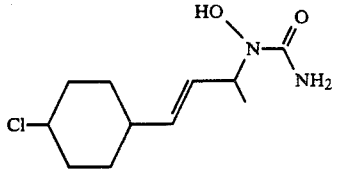 |
| 17 | 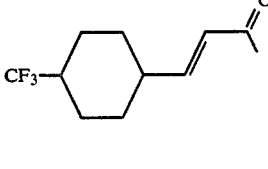 | 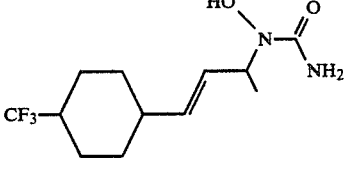 |
| 18 |  | 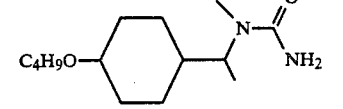 |
| 19 | 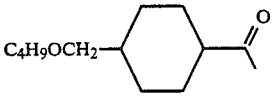 | 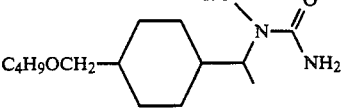 |
| 20 | 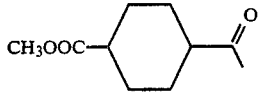 | 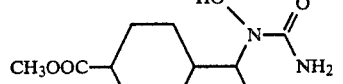 |
| 21 | 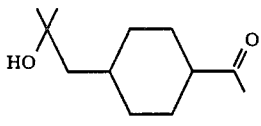 | 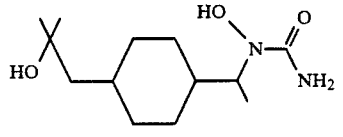 |
| 22 | 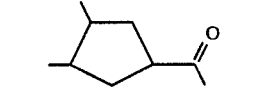 | 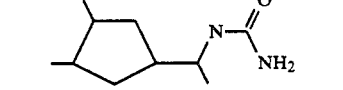 |
| 23 | 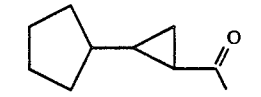 | 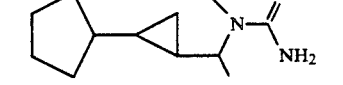 |
| 24 | 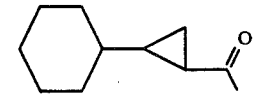 | 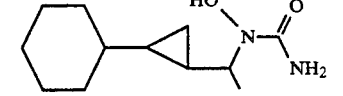 |
| 25 | 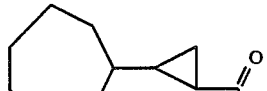 | 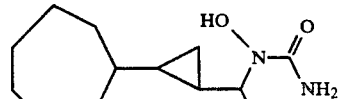 |
| 26 | 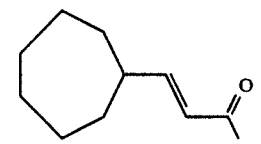 | 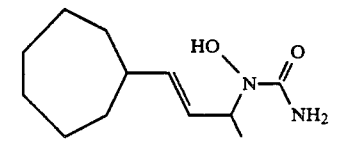 |

TABLE 3-continued

| Example | Carbonyl Precursor | Product |
|---|---|---|
| 27 | | |
| 28 | | |
| 29 | | |
| 30 | | |
| 31 | | |
| 32 | | |

The examples presented above are provided to enable one skilled in the art to practice the present invention, and are not to be read as limiting the scope of the invention as it is defined by the appended claims.

We claim:

1. A compound having the structure

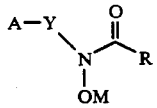

or a pharmaceutically acceptable salt thereof wherein
M represents hydrogen, a pharmaceutically acceptable cation, or a pharmaceutically acceptable metabolically cleavable group;
R is NR¹R² wherein
R¹ is selected from the group consisting of
hydrogen,
hydroxyl,
alkyl of from one to six carbon atoms,
hydroxyalkyl of from one to six carbon atoms, and
alkoxyalkyl in which the alkoxy portion and the alkyl portion each contain, independently, from one to six carbon atoms; and
R² is selected from the group consisting of
hydrogen,
alkyl of from one to six carbon atoms,
hydroxyalkyl of from one to six carbon atoms,
alkoxyalkyl in which the alkoxy and the alkyl portion each contain, independently, from one to six carbon atoms, and
alkanoyl of from two to eight carbon atoms;
A is selected from the group consisting of
(a) cycloalkyl of from three to eight carbon atoms, and
(b) optionally substituted cycloalkyl of from three to eight carbon atoms,
wherein the optional substituents on the cycloalkyl groups are selected from the group consisting of
alkyl of from one to six carbon atoms,
haloalkyl of from one to six carbon atoms,
alkoxy of from one to six carbon atoms,
alkoxyalkyl,
hydroxy, and
halogen; and
Y is selected from the group consisting of
alkylene of from one to six carbon atoms,
alkenylene of from two to six carbon atoms, and
cyclopropyl;
with the proviso that when A is cyclopropyl then Y is not alkylene.

2. A compound as defined by claim 1 having the structure

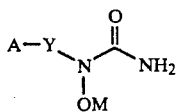

wherein

M represents hydrogen, a pharmaceutically acceptable cation, or a pharmaceutically acceptable metabolically cleavable group;

A is selected from the group consisting of
(a) cycloalkyl of from three to eight carbon atoms,
(b) cycloalkylene of from three to eight carbon atoms,
(c) optionally substituted cycloalkyl of from three to eight carbon atoms,
(d) optionally substituted cycloalkylene of from three to eight carbon atoms;
wherein the optional substitutents on the, cycloalkyl, and cycolalkylene groups are selected from the group consisting of
alkyl of from one to six carbon atoms,
haloalkyl of from one to six carbon atoms,
alkoxy of from one to six carbon atoms,
alkoxyalkyl,
hydroxy,
halogen,
carboxylic ester,
alkyl carboxylic ester;

Y is selected from the group consisting of
alkylene of from one to six carbon atoms,
alkenylene of from one to six carbon atoms, and
cyclopropyl;
with the proviso that when A is cyclopropyl then Y is alkenylene or cyclopropyl but not alkylene.

3. A compound as defined by claim 1 selected from the group consisting of
N-1-(trans-2-cyclopropylcycolpropylmethyl)-N-hydroxyurea;
N-cycolbutylmethyl-N-hydroxyurea;
N-cyclopentylmethyl-N-hydroxyurea;
N-cyclohexylmethyl-N-hydroxyurea;
N-cycloheptylmethyl-N-hydroxyurea;
N-1-(trans-2-cyclopropylcyclopropylethyl)-N-hydroxyurea;
N-1-(trans-2-cyclopropylcyclopropylethyl)-N-hydroxy-N'-methylurea;
N-1-(trans-2-cyclopropylcyclopropylethyl)-N-hydroxy-N'-phenylurea;
N-1-(trans-2-cyclopropylcyclopropylethyl)-N-hydroxy-N'-cyclohexylurea; and
or a pharmaceutically acceptable salt thereof.

4. A pharmaceutical composition for inhibiting the biosynthesis of leukotrienes comprising a therapeutically effective amount of a compound as defined by claim 1 in combination with a pharmaceutically acceptable carrier.

5. A method of inhibiting the biosynthesis of leukotrienes comprising administering to a mammal in need of such treatment a therapeutically effective amount of a compound as defined by claim 1.

* * * * *